United States Patent [19]

Bundy

[11] 4,104,476

[45] Aug. 1, 1978

[54] 3,7-INTER-m-PHENYLENE-4,5,6-TRINOR-9-DEOXY-9-METHYLENE-PGF-TYPE COMPOUNDS

[75] Inventor: Gordon L. Bundy, Portage, Mich.

[73] Assignee: The Upjohn Company, Kalamazoo, Mich.

[21] Appl. No.: 832,330

[22] Filed: Sep. 12, 1977

Related U.S. Application Data

[60] Division of Ser. No. 682,848, May 4, 1976, Pat. No. 4,060,534, which is a continuation-in-part of Ser. No. 651,622, Jan. 23, 1976, Pat. No. 4,021,467, which is a division of Ser. No. 556,768, Mar. 10, 1975, Pat. No. 3,950,363.

[51] Int. Cl.$^2$ ........................................... C07C 177/00
[52] U.S. Cl. ...................................... 560/61; 560/62; 560/55; 260/520 C; 260/520 R
[58] Field of Search .......................... 560/61, 62, 55; 260/520 C, 520 R

[56] References Cited

PUBLICATIONS

Derwent Abstract, 34317y/19, U.S. 4,021,467, 3/05/77.

Primary Examiner—Paul J. Killos
Attorney, Agent, or Firm—Robert A. Armitage

[57] ABSTRACT

This invention comprises certain analogs PGE or 11-deoxy-PGE the carbonyl at C-9 is replaced by methylene. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

61 Claims, No Drawings

3,7-INTER-m-PHENYLENE-4,5,6-TRINOR-9-DEOXY-9-METHYLENE-PGF-TYPE COMPOUNDS

The present application is a divisional application of Ser. No. 682,848, filed May 4, 1976, now issued as U.S. Pat. No. 4,060,534, on Nov. 29, 1977; which is a continuation-in-part of Ser. No. 651,622 filed Jan. 23, 1976, issued as U.S. Pat. No. 4,021,467 on May 3, 1977; which is a division of Ser. No. 556,768, filed Mar. 10, 1975, issued as U.S. Pat. No. 3,950,363 on Apr. 13, 1976.

The present invention relates to prostaglandin analogs, for which the essential material constituting disclosure therefor is incorporated by reference here from Ser. No. 628,848.

I claim:
1. A prostaglandin analog of the formula

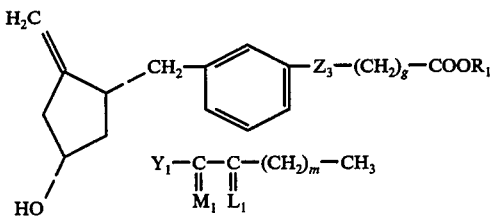

wherein $Z_3$ is oxa or methylene;
wherein $Y_1$ is trans—CH═CH—, —C≡C—, or —CH$_2$CH$_2$—; wherein $M_1$ is

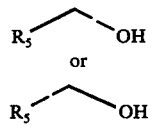

wherein $R_5$ is hydrogen or methyl;
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.
wherein $L_1$ is

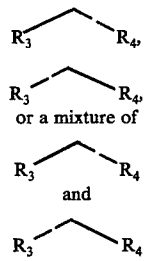

wherein $R_3$ and $R_4$ are hydrogen, methyl, or fluoro, being the same or different, with the proviso that one of $R_3$ and $R_4$ is fluoro only when the other is hydrogen or fluoro;
wherein $g$ is one, 2, or 3; and
wherein $m$ is one to 5, inclusive.

2. A prostaglandin analog according to claim 1, wherein $Y_1$ is —CH$_2$CH$_2$—.

3. A prostaglandin analog according to claim 2, wherein $M_1$ is

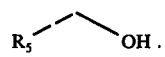

4. 3,7-inter-m-Phenylene-3-oxa-4,5,6-trinor-9-deoxy-9-methylene-15-epi-13,14-dihydro-PGF$_1$, a prostaglandin analog according to claim 3.

5. A prostaglandin analog according to claim 2, wherein $M_1$ is

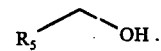

6. A prostaglandin analog according to claim 5, wherein $Z_3$ is oxa.

7. A prostaglandin analog according to claim 6, wherein $g$ is 3.

8. 3,7-inter-m-Phenylene-3-oxa-4,5,6-trinor-9-deoxy-9-methylene-2a,2b-dihomo-15-methyl-13,14-dihydro-PGF$_1$, a prostaglandin analog according to claim 7.

9. 3,7-inter-m-Phenylene-3-oxa-4,5,6-trinor-9-deoxy-9-methylene-2a,2b-dihomo-13,14-dihydro-PGF$_1$, a prostaglandin analog according to claim 7.

10. A prostaglandin analog according to claim 6, wherein $g$ is one.

11. A prostaglandin analog according to claim 10, wherein at least one of $R_3$ and $R_4$ is methyl.

12. A prostaglandin analog according to claim 11, wherein $R_3$ and $R_4$ are both methyl.

13. 3,7-inter-m-Phenylene-3-oxa-4,5,6-trinor-9-deoxy-9-methylene-16,16-dimethyl-13,14-dihydro-PGF$_1$, a prostaglandin analog according to claim 12.

14. A prostaglandin analog according to claim 10, wherein at least one of $R_3$ and $R_4$ is fluoro.

15. A prostaglandin analog according to claim 14, wherein $R_3$ and $R_4$ are both fluoro.

16. 3,7-inter-m-Phenylene-3-oxa-4,5,6-trinor-9-deoxy-9-methylene-16,16-difluoro-13,14-dihydro-PGF$_1$, a prostaglandin analog according to claim 15.

17. A prostaglandin analog according to claim 10, wherein $R_3$ and $R_4$ are both hydrogen.

18. A prostaglandin analog according to claim 17, wherein $R_5$ is methyl.

19. 3,7-inter-m-Phenylene-3-oxa-4,5,6-trinor-9-deoxy-9-methylene-15-methyl-13,14-dihydro-PGF$_1$, a prostaglandin analog according to claim 18.

20. A prostaglandin analog according to claim 17, wherein $R_5$ is hydrogen.

21. 3,7-inter-m-Phenylene-3-oxa-4,5,6-trinor-9-deoxy-9-methylene-13,14-dihydro-PGF$_1$, a prostaglandin analog according to claim 20.

22. A prostaglandin analog according to claim 1, wherein $Y_1$ is —C≡C—.

23. A prostaglandin analog according to claim 22, wherein $M_1$ is

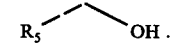

24. 3,7-inter-m-Phenylene-3-oxa-4,5,6-trinor-9-deoxy-9-methylene-15-epi-13,14-didehydro-PGF$_1$, a prostaglandin analog according to claim 23.

25. A prostaglandin analog according to claim 22, wherein $M_1$ is

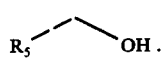

26. A prostaglandin analog according to claim 25, wherein $Z_3$ is oxa.

27. A prostaglandin analog according to claim 26, wherein $g$ is 3.

28. 3,7-inter-m-Phenylene-3-oxa-4,5,6-trinor-9-deoxy-9-methylene-2a,2b-dihomo-15-methyl-13,14-didehydro-$PGF_1$, a prostaglandin analog according to claim 27.

29. 3,7-inter-m-Phenylene-3-oxa-4,5,6-trinor-9-deoxy-9-methylene-2a,2b-dihomo-13,14-didehydro-$PGF_1$, a prostaglandin analog according to claim 27.

30. A prostaglandin analog according to claim 26, wherein $g$ is one.

31. A prostaglandin analog according to claim 30, wherein at least one of $R_3$ and $R_4$ is methyl.

32. A prostaglandin analog according to claim 31, wherein $R_3$ and $R_4$ are both methyl.

33. 3,7-inter-m-Phenylene-3-oxa-4,5,6-trinor-9-deoxy-9-methylene-16,16-dimethyl-13,14-didehydro-$PGF_1$, a prostaglandin analog according to claim 32.

34. A prostaglandin analog according to claim 30, wherein at least one of $R_3$ and $R_4$ is fluoro.

35. A prostaglandin analog according to claim 34, wherein $R_3$ and $R_4$ are both fluoro.

36. 3,7-inter-m-Phenylene-3-oxa-4,5,6-trinor-9-deoxy-9-methylene-16,16-difluoro-13,14-didehydro-$PGF_1$, a prostaglandin analog according to claim 35.

37. A prostaglandin analog according to claim 30, wherein $R_3$ and $R_4$ are both hydrogen.

38. A prostaglandin analog according to claim 37, wherein $R_5$ is methyl.

39. 3,7-inter-m-Phenylene-3-oxa-4,5,6-trinor-9-deoxy-9-methylene-15-methyl-13,14-didehydro-$PGF_1$, a prostaglandin analog according to claim 38.

40. A prostaglandin analog according to claim 37, wherein $R_5$ is hydrogen.

41. 3,7-inter-m-Phenylene-3-oxa-4,5,6-trinor-9-deoxy-9-methylene-13,14-didehydro-$PGF_1$, a prostaglandin analog according to claim 40.

42. A prostaglandin analog according to claim 1, wherein $Y_1$ is trans—CH=CH—.

43. A prostaglandin analog according to claim 42, wherein $M_1$ is

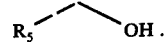

44. 3,7-inter-m-Phenylene-3-oxa-4,5,6-trinor-9-deoxy-9-methylene-15-epi-$PGF_1$, a prostaglandin analog according to claim 43.

45. A prostaglandin analog according to claim 42, wherein $M_1$ is

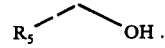

46. A prostaglandin analog according to claim 45, wherein $Z_3$ is oxa.

47. A prostaglandin analog according to claim 46, wherein $g$ is 3.

48. 3,7-inter-m-Phenylene-3-oxa-4,5,6-trinor-9-deoxy-9-methylene-2a,2b-dihomo-15-methyl-$PGF_1$, a prostaglandin analog according to claim 47.

49. 3,7-inter-m-Phenylene-3-oxa-4,5,6-trinor-9-deoxy-9-methylene-2a,2b-dihomo-$PGF_1$, a prostaglandin analog according to claim 47.

50. A prostaglandin analog according to claim 46, wherein $g$ is one.

51. A prostaglandin analog according to claim 50, wherein at least one of $R_3$ and $R_4$ is methyl.

52. A prostaglandin analog according to claim 51, wherein $R_3$ and $R_4$ are both methyl.

53. 3,7-inter-m-Phenylene-3-oxa-4,5,6-trinor-9-deoxy-9-methylene-16,16-dimethyl-$PGF_1$, a prostaglandin analog according to claim 52.

54. A prostaglandin analog according to claim 50, wherein at least one of $R_3$ and $R_4$ is fluoro.

55. A prostaglandin analog according to claim 54, wherein $R_3$ and $R_4$ are both fluoro.

56. 3,7-inter-m-Phenylene-3-oxa-4,5,6-trinor-9-deoxy-9-methylene-16,16-difluoro-$PGF_1$, a prostaglandin analog according to claim 55.

57. A prostaglandin analog according to claim 50, wherein $R_3$ and $R_4$ are both hydrogen.

58. A prostaglandin analog according to claim 57, wherein $R_5$ is methyl.

59. 3,7-inter-m-Phenylene-3-oxa-4,5,6-trinor-9-deoxy-9-methylene-15-methyl-$PGF_1$, a prostaglandin analog according to claim 58.

60. A prostaglandin analog according to claim 57, wherein $R_5$ is hydrogen.

61. 3,7-inter-m-Phenylene-3-oxa-4,5,6-trinor-9-deoxy-9-methylene-$PGF_1$, a prostaglandin analog according to claim 60.

* * * * *

UNITED STATES PATENT OFFICE
CERTIFICATE OF CORRECTION

Patent No. 4,104,476                        Dated August 1, 1978

Inventor(s) Gordon L. Bundy

It is certified that error appears in the above-identified patent and that said Letters Patent are hereby corrected as shown below:

Column 1, line 15, "Ser. No. 628,848" should read -- U.S. Pat. No. 4,050,534 --.

Column 1, lines 23-26, that portion of the formula reading

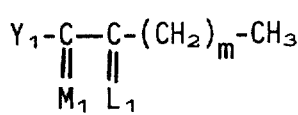     should read     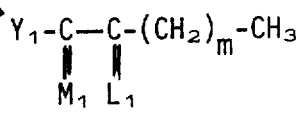

Column 4, lines 12-14,

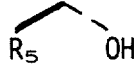     should read     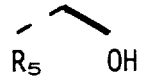

Signed and Sealed this

Twentieth Day of March 1979

[SEAL]

Attest:

RUTH C. MASON
*Attesting Officer*

DONALD W. BANNER
*Commissioner of Patents and Trademarks*